United States Patent
Trung et al.

(10) Patent No.: US 6,551,451 B2
(45) Date of Patent: Apr. 22, 2003

(54) METHOD FOR DETERMINING LIQUID CONTENT IN CHEMICAL PULPS USING RAMEN SPECTROMETRY

(75) Inventors: Thanh P. Trung, Vancouver (CA); Denys Leclerc, Vancouver (CA)

(73) Assignee: Pulp and Paper Research Institute of Canada, Pointe Claire (CA)

(*) Notice: Subject to any disclaimer, the term of this patent is extended or adjusted under 35 U.S.C. 154(b) by 17 days.

(21) Appl. No.: 09/740,018

(22) Filed: Dec. 20, 2000

(65) Prior Publication Data

US 2001/0017195 A1 Aug. 30, 2001

Related U.S. Application Data

(60) Provisional application No. 60/171,614, filed on Dec. 23, 1999.

(30) Foreign Application Priority Data

Jan. 20, 2000 (JP) .......................................... 2000-011608
Feb. 15, 2000 (JP) .......................................... 2000-036904

(51) Int. Cl.[7] .......................... D21C 7/12; G01N 21/65
(52) U.S. Cl. ........................ 162/49; 356/317; 356/318; 356/326; 356/417
(58) Field of Search ........................ 162/49, 50, 198, 162/263; 356/317, 326, 318, 331, 417

(56) References Cited

U.S. PATENT DOCUMENTS

| 5,302,248 A | 4/1994 | Weinstock et al. |
| 5,486,915 A | 1/1996 | Jeffers et al. |
| 5,842,150 A | 11/1998 | Renberg |

FOREIGN PATENT DOCUMENTS

| DE | 196 53 539 | 7/1998 |
| WO | WO 95 26438 | 10/1995 |
| WO | WO 98/28488 | 7/1998 |

OTHER PUBLICATIONS

Weinstock I. A. et al, Fourier Transform Raman Spectroscopic Studies of a Novel Wood Pulp Bleaching System, May 1, 1993, XP000647003.

"G–18—Kappa Number of Pulp", Standard Methods of the Technical Section of the CPPA, Montreal, "T–236—Kappa Number of Pulp", TAPPI Standards Methods, TAPPI PRESS, Atlanta.

(List continued on next page.)

Primary Examiner—Steve Alvo
(74) Attorney, Agent, or Firm—Ogilvy Renault (57) ABSTRACT

A rapid method is provided for the on-line spectroscopic determination of lignin content and/or kappa number in wood pulps. Unlike currently available commercial instrumentation, the method enables one to measure lignin content independently of species variations and pulp consistency. The method includes the steps of: (1) withdrawing high-consistency samples of wood pulp from a chemical pulp manufacturing process; (2) subjecting these samples to a monochromatic visible-light source; (3) recording the resulting scattered light and its Raman spectrum over a predetermined range of wave numbers so as to produce Raman-scattered light intensity measurements; (4) determining either the uncorrected, baseline-corrected and/or integrated Raman-scattered light intensity of the samples over a predetermined range of wavenumbers shown by different combinations of lignin content, cellulose content, and consistency; (5) correlating by either univariate or multivariate calibration the relationships between the Raman-scattered light intensity measurements of unknown samples and the Raman-scattered light intensity shown by known combinations of lignin content, cellulose content, and consistency so that the lignin content and/or kappa number in wood pulps can be accurately determined over a Kappa range of 5 to 110 and preferably 5 to 20, for any levels of sample cellulose content or pulp consistency.

21 Claims, 8 Drawing Sheets

OTHER PUBLICATIONS

Vroom, K.E., Pupl Paper Mag. Can., 58(3):228–231 (1957).

Wells, C. "II Chemical Pulping Area", in Pulp and Paper Manufaacture (3rd Ed.) vol. 10 Mill–wide Process Control & Information Systems, TAPPI/CPPA, Atlanta/Montreal, 1983, pp. 79–123.

Yeager, R., Pulp and Paper, Sep. 1998, 87–88, 91–92.

Kubulnieks et al, Tappi J. 70(11) 38–42 (1987).

Bentley, R. G., SPIE Proceedings, vol. 665, p. 265–279 (1986).

Marton, J., Sparks, H.E., Tappi J., 50(7), 363–368 (1967).

Berben, S.A., Rademacher, J.P., Sell, L.O., Easty, D.B., Tappi J. 70(11), 129–133 (1987).

Haaland, D.M. and Thomas. E.V., Anal. Chem., 60(10):1193–1202 (1988); Anal. Chem. 60(10):1202–1208 (1998).

Yusak, E., Lohrke, C., Proc. 1993 TAPPI Pulp. Conf., 663–671.

Honeywell–Measurex (PulpStar) (Trademark).

Liljenberg, T. Backa, S. Lindberg, J., Dahlquist, E., Proceedings of the 10th Biannial ISWPC vol. 3, 266–69 Yokohama, Jun. 7–10, 1999.

Atalla, R.H., Agarwal, U.P., Bond, J.S. 4.6 Raman Spectroscopy, in Lin, S.W., Dence C. W. eds., Methods in Lignin Chemistry, Springer–Verlag, Berlin, 162–176 (1992).

Agarwal, U.P., Atalla, R.H., 8–Raman Spectroscopy, in Conners, T.E., Banerjee, S. eds. Surface Analysis of Paper, CRC Press, Inc., Boca Raton, Fl. 152–181 (1995).

Agarwal, U.P., Chapter 9, An Overview of Raman Spectroscopy as Applied to Lignocellulosic Materials, in ARGYROPOULOS, D.S., Advances in Lignocellulosics Characterization, Tappi Press, Atlanta, GA. 201–225 (1999).

Kenton, R.C., Rubinovitz, R.L. Appl. Spectrosc. 44(8), 1377–11380 (1990).

Evans, P.A. Spectrochemica Acta, 47A (9/10), 1441–1447 (1991).

Lewis, I.R., Daniel, N.W., Jr., Chaffin, N.C., Griffiths, P.R., Spectrochemica Acta, 50A (11), 1943–1958 (1994).

Takayama, M., Johjima, T., Yamanaka, T. Wariishi, H., Tanaka, H., Spectrochemica Acta, 53A, 1621–1628 (1997).

Agarwal, U.P., Ralph, S.A., appl. Spectrosc., 51 (11), 1648–1655 (1997).

Agarwal, U.P. Weinstock, I.A., Proceedings of the 1996 International Pulp Bleaching Conference, 531–535.

Sukhov, D.A. Evstigneyev E.I., Derkacheva, O. Yu, Nabiev, I.R. Kaptsov, A.H. Proceedings of the 7th International Symposium on wood and Pulping Chemistry, vol. 2, 969–974, (1993).

Ibrahim, A., Oldham, P.B. Conners, T.E. Shultz, T.P., Microchemical Journal, 56, 393–402 (1997).

Sun, Z., Ibraham, A., Oldham, P.B., J. Agric. Food Chem. 45, 3088–91 (1997).

METHOD FOR DETERMINING LIQUID CONTENT IN CHEMICAL PULPS USING RAMEN SPECTROMETRY

CROSS-REFERENCE TO RELATED APPLICATION

This Application claims priority under 35 U.S.C. 119(e) from U.S. Provisional Application Ser. No. 60/171,614, filed Dec. 23, 1999.

BACKGROUND OF THE INVENTION i) Field of the Invention

This invention relates generally to an on-line method for determining lignin content and/or kappa number in wood pulp samples during the pulping and bleaching operations of a mill. The invention specifically relates to the application of visible-light Raman spectrometry for measuring the Raman-scattered light intensity of pulp samples containing variable amounts of lignin and cellulose.

ii) Description of Prior Art

In a chemical pulp manufacturing process, the production of pulp and/or paper products from wood chips is effected by either partially or entirely removing lignin from the wood prior to the manufacture of pulp/paper sheets. Lignin is a polymeric chemical compound that binds wood fibers together. The most common method of lignin removal is by chemical means, whereby wood chips and chemicals are combined and cooked together at controlled temperature and pressure in a vessel known as a digester. In the kraft process, lignin removal is performed by cooking wood chips in highly alkaline liquor called white liquor, which selectively dissolves lignin and releases the cellulosic fibers from their wooden matrix. The white liquor typically contains caustic soda, sodium sulphide and sodium carbonate. The extent of lignin removal is measured in terms of the blow-line Kappa number ["G-18-Kappa Number of Pulp", Standard Methods of the Technical Section of the CPPA, Montreal; "T-236-Kappa Number of Pulp", TAPPI Standard Methods, TAPPI PRESS, Atlanta]. This method is performed in the laboratory and takes approximately thirty minutes. The blow-line Kappa number is then used for controlling the pulping operation and for estimating the charge of chemicals used for bleaching without producing waste. Furthermore, mill personnel need reliable Kappa-number values to avoid excessive delignification and fibre degradation during the oxygen-delignification stage. Batch digesters control strategies use feedforward control, and rely on keeping the chip and white liquor feeds at levels predetermined by the overall production rate. Kappa number targets are calculated with the use of the H-factor [VROOM, K. E., Pulp Paper Mag. Can., 58(3):228–231 (1957)]. The temperature profile of the cook is adjusted approximately halfway through the cook after determining the blow-line kappa number with the laboratory method, which introduces a 30-minute delay, thereby producing significant process variability. Such a delay is incompatible with control strategies requiring timely analysis of pulp properties. Continuous digesters can be controlled more precisely by adding a feedback control loop around the lower cooking zone, but the control strategy must still allow for the dead time introduced by the laboratory method [WELLS, C. "VII Chemical Pulping Area", in Pulp and Paper Manufacture (3rd Ed.) Vol. 10 Mill-wide Process Control & Information Systems, TAPPI/CPPA, Atlanta/Montreal, 1983, pp. 79–123]. The ongoing development of modern chemical pulping and bleaching processes has thus underscored the need for a real-time Kappa number sensor which would provide the timely information towards better control of pulping and bleaching operations and a more efficient use of the chemicals involved in the process.

In order to fill this need, several automated analysers are available commercially. These analysers measure the optical properties of pulp suspensions by a variety of methods that use different regions of the electromagnetic spectrum. The current generation of analysers uses the strong absorption of lignin in the ultraviolet region of the spectrum as a basis for kappa-number measurement. For example, many current Kappa number analysers use UV light with a combination of reflectance, scattering and transmittance measurements [YEAGER, R., Pulp and Paper, September 1998, 87–88, 91–92: BTG KNA 5100 (reflection); Kubulnieks et al., Tappi J. 70(11) 38–42 (1987): STFI OptiKappa™ ABB Analyzer (absorption)]. Although the principle is simple, the actual measurement is complex for both of these methods because the lignin absorption cannot be measured accurately without accounting for interferences from light scattering and reflectance artifacts produced by variations in pulp consistency, as well as by the physical characteristics of the fibres. This problem can be addressed by building calibrations that are valid for a relatively narrow range of sampling conditions and furnishes. These calibrations invariably fail during process upsets and rapid changes in furnish. Calibration is done by characterising the relationship between the three types of measurement at a given consistency. These types of sensing devices are very sensitive to consistency variations. Reliable samples from the mid-digester and blow-line sampling points cannot be obtained because the consistency of the samples is then outside the range allowed for by the two-point UV calibration procedure. Although the calibration works well for bleach-plant samples [YEAGER, R., Pulp and Paper, September 1998, 87–88,91–92] and for single-species furnishes and mixed furnishes of constant composition, the sensors do not provide accurate results for furnishes of unknown or rapidly changing composition [BENTLEY, R. G., SPIE Proceedings, Vol. 665, p. 265–279 (1986)]. Moreover, maintenance of the two-point calibration procedure and of the sampling system requires constant attention from mill personnel. For example, the instrument has to be re-calibrated every time when either the source or the electronics are replaced, by using a wide variety of kappa-number pulp samples. This involves time-consuming trial and error and tweaking the process, during which period the mill have to rely on manual analysis. Furthermore, when the composition of chips is constantly changing, instruments have to be constantly re-calibrated to keep up with the changes in furnish, which is a considerably time-consuming exercise. Also, the complexity of the sampling system makes current analysers very sensitive to variations in water quality and variations in sample consistency. In addition, sample throughput is relatively low, achieving about two samples per hour for each location.

Since lignin also has well-defined infrared absorption bands, the use of the mid-infrared region has been proposed in the past by many investigators as a means to overcome this problem. For example, the kappa number of pulps was determined by using the lignin peak at 1510 $cm^{-1}$ and a cellulose peak as an internal standard [MARTON, J., SPARKS, H. E., Tappi J., 50 (7), 363–368 (1967)]. The lignin/cellulose peak-area ratio was found to be insensitive to variations in basis weight. Also, another method was developed with the use of DRIFTS for estimating lignin in unbleached pulp [BERBEN, S. A., RADEMACHER, J. P., SELL, L. O., EASTY, D. B., Tappi J.,70(11), 129–133

(1987)]. Lignin-free cotton linters were used as the reference material. A lignin spectrum is thus obtained after spectral subtraction of the cellulose contribution. A linear relationship is found between the area of the band at 1510 cm$^{-1}$ and kappa number for a wide variety of species. The relationship holds for a range of hardwood and softwood pulp having Kappa numbers ranging from 10 to 120. However, these methods used dry pulp samples. Mid-infrared methods are not amenable to on-line kappa number determination because of the presence of large and variable amounts of water in mill samples, which interferes with lignin determination.

The use of the near-infrared region has also been proposed as a means of eliminating this limitation. Advantages over previous techniques include: no sample preparation, short measurement times, relatively long optical paths and the possibility of using fiber-optic technology for real-time, in situ measurements. Water peaks in this region are smaller and do not affect kappa measurements. Multivariate calibration methods such as PCA or PLS are used to account for species variability. Also, temperature effects and interferences by other cations and anions can be modelled in this spectral region through the use of partial least-squares (PLS) multi-component calibration techniques. PLS is a multi-component calibration method that is well known in the art [HAALAND, D. M. and THOMAS, E. V., Anal. Chem., 60(10):1193–1202 (1988); Anal. Chem., 60(10):1202–1208 (1988)]. This method enables one to build a spectral model, which assumes that the absorbance produced by a species is linearly proportional to its concentration. However, this method only works well with dried pulp, and attempts to adapt it to dewatered pulp have failed because of baseline artefacts produced by variations in water content [YUSAK, E., LOHRKE, C., Proc. 1993 TAPPI Pulp. Conf., 663–671]. Commercial instruments based on NIR reflectance measurements are nevertheless available from Honeywell-Measurex (PulpStar™) [web site: www.iac.honeywell.com] and from Asea Brown Boveri (ABB) [Proceedings of the 10$^{th}$ Biennial ISWPC Vol. 3 266–69 Yokohama, June7–10 1999]. Jeffers et al [U.S. Pat. No. 5,486,915] describes a method for on-line measurement of lignin in wood pulp by color shift of fluorescence. Although the sampling system is simple, the method is sensitive to species variability and thus unsuitable for analysis of variable pulp furnishes.

Raman spectroscopy is a technique that measures the intensity of light produced by the inelastic scattering of photons originating from a monochromatic light source such as a visible-light laser. This inelastic scattering occurs with a small frequency shift with respect to the frequency of the light source. The Raman effect generates a spectrum that is similar to that of an infrared spectrum, but where only the absorption bands that are produced by symmetric-mode vibrations are present. The mid-infrared water band that usually interferes with lignin measurements is thus no longer active. Unlike the ultraviolet region that is sensitive to light scattered and reflected by the pulp fibres, the Raman signal should not be affected by the physical characteristics of these fibres such as coarseness. Atalla et al. have discussed the challenges posed by early applications of conventional Raman spectroscopy to lignin-containing samples [ATALLA, R. H., AGARWAL, U. P., BOND, J. S., 4.6 Raman Spectroscopy, in LIN, S. Y., DENCE, C. W. eds., Methods in Lignin Chemistry, Springer-Verlag, Berlin, 162–176 (1992)]. It is well known in the art that lignin produces a strong fluorescence background, thereby obscuring its Raman spectrum. Very noisy Raman spectra are obtained, even after many hours of data acquisition, and these are thus unsuitable for on-line applications. The state of the art regarding pulp and paper applications of Raman spectrometry was reviewed a few years ago by Agarwal and Atalla [AGARWAL, U. P., ATALLA, R. H., 8—Raman Spectroscopy, in CONNERS, T. E., BANERJEE, S. eds., Surface Analysis of Paper, CRC Press, Inc., Boca Raton Fla., 152–181 (1995)], and more recently by Agarwal [AGARWAL, U. P., Chapter 9: An Overview of Raman Spectroscopy as Applied to Lignocellulosic Materials, in ARGYROPOULOS, D. S., Advances in Lignocellulosics Characterization, Tappi Press, Atlanta Ga., 201–225 (1999)]. According to Agarwal and Atalla, using red or near-infrared excitation and measuring the back-scattered light, one can analyse lignin-containing samples by minimizing sample laser-induced fluorescence and heating, but at the expense of the Raman signal. The much weaker Raman signal can still be enhanced by the use of a Fourier transform spectrometer, but a much longer acquisition time than that suitable for on-line analysis is needed. Increasing the laser power enhances the Raman signal, but increases the likelihood of sample bleaching, especially at longer acquisition times. Investigators have nevertheless used FT-NIR Raman to characterise wood samples [KENTON, R. C., RUBINOVITZ, R. L., Appl. Spectrosc. 44 (8), 1377–1380 (1990); EVANS, P. A., Spectrochemica Acta, 47A (9/10), 1441–1447 (1991); LEWIS, I. R., DANIEL, N. W., jr., CHAFFIN, N. C., GRIFFITHS, P. R., Spectrochemica Acta, 50A (11), 1943–1958 (1994); TAKAYAMA, M., JOHJIMA, T., YAMANAKA, T., WARIISHI, H., TANAKA, H., Spectrochemica Acta, 53A, 1621–1628 (1997); AGARWAL, U. P. RALPH, S. A., Appl. Spectrosc., 51 (11), 1648–1655 (1997)]. Even so, for wood samples, the fluorescence is very significant and still overcomes the Raman bands. FT-NIR Raman investigations have also been performed on pulp: samples were ground up, diluted with potassium bromide (KBr) and either made into KBr pellets [AGARWAL, U. P., WEINSTOCK, I. A., Proceedings of the 1996 International Pulp Bleaching Conference, 531–535], or immersed in alcohol prior to analysis [SUKHOV, D. A., EVSTIGNEYEV, E. I., DERKACHEVA, O. YU, NABIEV, I. R., KUPTSOV, A. H., Proceedings of the 7$^{th}$ International Symposium on Wood and Pulping Chemistry, Volume 2, 969–974 (1993)] so as to reduce the fluorescence, especially for samples with higher lignin content. Direct analysis of damp pulp samples of diverse western softwood species has also been performed by Ibrahim et al. [IBRAHIM, A., OLDHAM, P. B., CONNERS, T. E., SHULTZ, T. P., Microchemical Journal, 56, 393–402 (1997)]. Data acquisition for each sample took about 15 minutes, a time much too long for a realistic on-line application with multiple sample points. The acquisition time could be shortened if the data obtained was of high quality, with low scatter and no systematic bias. In the abstract of that paper, Ibrahim et. al. claim that a linear relationship is obtained over a range of Kappa numbers between 10 and 38. However, the data shown in FIG. 4 of Ibrahim et al. suffers from a "sigmoidal-like systematic error", and is fact very far from a line, especially at Kappa numbers between 10 and 15. This prevents an accurate determination of lignin content below Kappa numbers of 15. Also, the Raman signal is affected by detector noise for pulps having Kappa numbers below 10, thereby preventing any meaningful application of this technique to either $O_2$ delignification or bleach-plant control. Sun et al. [SUN, Z., IBRAHIM, A., OLDHAM, P. B., J. Agric. Food Chem. 45,3088–91 (1997)] obtained similar results for dry hardwood samples over a range of Kappa numbers between 4 and 20, whereby the relative standard deviation was found to be about 10% for samples having Kappa numbers below 10. Finally, the data is very scattered for softwoods above a Kappa number of 15 probably because of significant fluorescence interference and/or sample bleaching, thereby rendering the FT-NIR Raman technique useless for digester control. Therefore, the presence of even more intense fluorescence produced by lignin chromophores when using visible-light excitation seemingly creates an insurmountable obstacle: a large, species-dependent fluorescence background would then swamp the Raman signal, thereby making it unusable for on-line application on mixed furnishes. Furthermore, acquisition times requiring several hours are required for reducing the noise of the Raman portion of the spectrum. No indication was given by any of the aforementioned investigators as to how to reduce the fluorescence background or to perform adequate measurements of lignin content at low or moderate Kappa numbers. Agarwal and Atalla have stated [AGARWAL, U. P., ATALLA, R. H., 8—Raman Spectroscopy, in CONNERS, T. E., BANERJEE, S. eds., *Surface Analysis of Paper*, CRC Press, Inc., Boca Raton Fla., 152–181 (1995)] that one cannot use visible-light excitation to perform quantitative lignin content measurements with Raman spectroscopy because of laser-induced fluorescence (LIF) in pulp samples, as well as pre-resonance effects produced by a small minority of lignin chromophores that distort the lignin signal by enhancing the contribution of only part of the lignin available. Agarwal has discussed these effects in detail [AGARWAL, U. P., Chapter 9: An Overview of Raman Spectroscopy as Applied to Lignocellulosic Materials, in ARGYROPOULOS, D. S., *Advances in Lignocellulosics Characterization*, Tappi Press, Atlanta Ga., 201–225 (1999)]. Therefore, a person skilled in the art would be discouraged from analysing pulp samples for lignin content with visible-light excitation, because of the presence of non-resonance effects and a much stronger fluorescence background than that found in the near-infrared region.

Therefore, none of the methods cited in the prior art constitutes a simple reliable on-line method capable of accurately measuring the residual lignin in wood pulps irrespective of wood species or consistency variations, at Kappa numbers below 15. Such a method would feature a stable calibration which would not drift or be sensitive to wood species or variation in pulp consistency. In the following, we disclose such a method.

SUMMARY OF THE INVENTION

It is an object of this invention to provide a method for determining lignin and/or kappa number in wood pulp during pulping and bleaching operations of a pulp manufacturing process.

It is a specific object of the invention to provide such a method employing the Ramon spectrum of the pulp.

In accordance with the invention there is provided a method for determining lignin content and/or kappa number in a wood pulp sample during pulping and bleaching operations of a chemical pulp manufacturing process, comprising the steps of: a) withdrawing a plurality of high consistency samples of wood pulp from a chemical pulp manufacturing process; b) subjecting said plurality of samples to a monochromatic visible-light source, and allowing the samples to scatter said visible light; c) determining the Raman spectrum of the scattered visible light over a predetermined range of wave numbers to produce Raman-scattered light intensity measurements; and d) comparing the Raman-scattered light intensity measurements of said plurality of samples with the Raman-scattered light intensity measurements shown by known combinations of lignin content, cellulose content and consistency and evaluating the lignin content and/or kappa number of said wood pulp therefrom.

DISCLOSURE OF THE INVENTION

The present invention provides a rapid method for determining lignin or kappa number in wood pulps. This method overcomes the disadvantages previously discussed. The method enables one to measure lignin content and/or kappa number independently of species variations and pulp consistency.

The method has application for determining kappa number of wood pulp in a range of 5 to 1 10 kappa, preferably 5 to 15 kappa.

The method is suitably employed with pulp suspensions having a consistency of 15 to 30%.

The comparison step d) suitably comprises evaluating by univariate or multivariate calibration, relationships between the Raman-scattered light intensity measurements of the plurality of samples and the Raman-scattered light intensity measurements shown by the known combinations of lignin content, cellulose content and consistency.

The Ramon-scattered light intensity measurements of the known combinations of lignin content, cellulose content and consistency may suitably be determined as an uncorrected, baseline corrected or integrated Raman-scattered light intensity over a predetermined range of wave numbers.

Suitably the Raman-scattered light intensity measurements are carried out within a range of wave number shift situated from 1000 to 2000 $cm^{-1}$, with respect to the excitation frequency.

The laser excitation for the measurements is suitably carried out over the visible wavelength range situated between 700 and 850 nm.

The spectrophotometry for the measurements is suitably performed with visible-light scattering measurements; and a fiber-optic excitation/collection probe is used in the spectrophotometry. The spectrophotometry may be performed in a flow-through cell for continuous measurements.

The relationships between the Raman-scattering measurements of the samples under investigation and the corresponding measurements of the known samples employed in the comparison of step d) of the method can conveniently be obtained with the use of partial least-squares (PLS) multivariate calibrations.

The method can be performed using a laser power setting that is low enough to prevent sample bleaching. A simple washing cycle with either water or preferably a mildly alkaline water solution may be provided. Since data acquisition only takes a few seconds, a high sample throughput will allow many process streams to be multiplexed to a single analyzer through either the use of fiber optics or a multiple-stream sampling system.

The analysis method described below uses Raman-scattered light intensity measurements obtained from the Raman spectra of pulp samples illuminated by the monochromatic light emitted by a visible-light laser. These measurements are generally free from water interference. The integrated Raman-scattered light intensity of the pulp is measured along predetermined spectral regions around 1600 $cm^{-1}$ for lignin and around 1100 $cm^{-1}$ for cellulose. Alternatively, the Raman-scattered light-intensity spectrum can be normalized to the value of the Raman-scattered light intensity around 1100 $cm^{-1}$ so as to mimic the lignin/ cellulose integrated intensity ratio. With the aid of a partial least squares (PLS) calibration, the normalized lignin/cellulose intensity ratio for each sample is made to correlate directly with the lignin concentration obtained from the standard-method laboratory analysis described previously. This correlation is generated by supplying spectra of known pulp samples to training software, which then develops a model for the spectral region being used. Although not necessary, it is generally preferable that the concentration of all pulp components be accounted for within a PLS calibration so that the lignin measurements are accurate and without bias, thereby creating a noise-free model that can be characterised with a small number of basis vectors. The model then uses these basis vectors for characterising components in unknown samples. The lignin content and/or Kappa number of the pulp sample is then calculated with the PLS model. Selected pulp process samples are also analyzed with standard analytical methods (CPPA G. 18) so as to establish a more reliable calibration set with the mill data obtained by Raman spectrophotometry. Visible-light Raman lignin measurements could then be used for reducing the process variability of pulping and bleaching operations. The application of this invention to pulp and paper liquors provides a method for determining lignin content and/or Kappa number that is faster, more reliable, and requires less maintenance than existing methods. In summary, this new method replaces currently used UV or NIR sensors, and addresses the previously discussed shortcomings of these devices.

In one particular embodiment the present invention provides a method for the on-line spectroscopic determination of lignin content and/or kappa number in wood pulps. Unlike currently available commercial instrumentation, the method enables one to measure lignin content independently of species variations and pulp consistency. The method includes the steps of: (1) withdrawing high-consistency samples of wood pulp from a chemical pulp manufacturing process; (2) subjecting these samples to a monochromatic visible-light source; (3) recording the resulting scattered light and its Raman spectrum over a predetermined range of wave numbers so as to produce Raman-scattered light intensity measurements; (4) determining either the uncorrected, baseline-corrected and/or integrated Raman-scattered light intensity of the samples over a predetermined range of wavenumbers shown by different combinations of lignin content, cellulose content, and consistency; (5) correlating by either univariate or multivariate calibration the relationships between the Raman-scattered light intensity measurements of unknown samples and the Raman-scattered light intensity shown by known combinations of lignin content, cellulose content, and consistency so that the lignin content and/or kappa number in wood pulps can be accurately determined over a Kappa range of 5 to 110, preferably 5 to 20 and more preferably 5 to 15, for any levels of sample cellulose content or pulp consistency.

BRIEF DESCRIPTION OF THE DRAWINGS

In drawings which illustrates embodiments of the present invention.

METHOD FOR CARRYING OUT THE INVENTION

Figure 1:
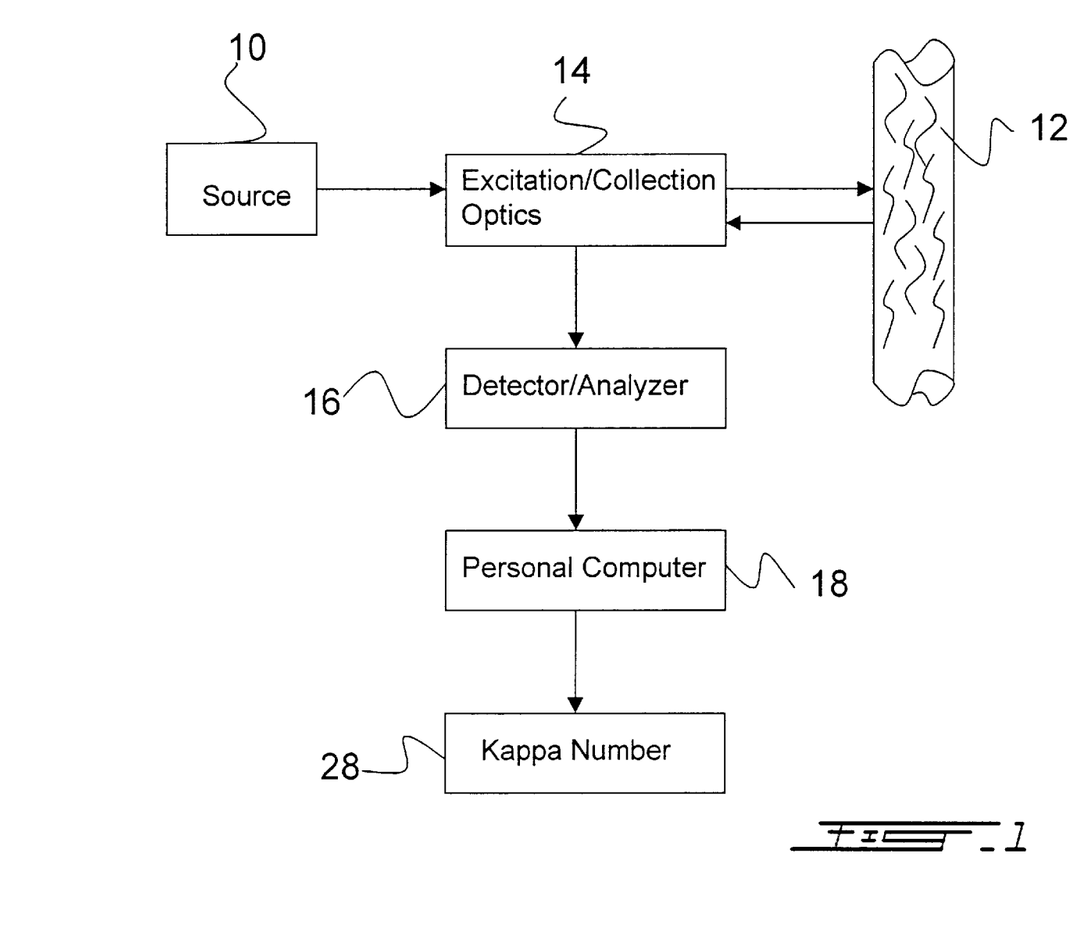
FIG. 1 is a diagrammatic view of a sensing apparatus according to one embodiment of the present invention.

FIG. 1 is a diagrammatic view of a sensing apparatus according to one embodiment of the present invention. Referring to FIG. 1, excitation light from a visible light source 10 is delivered to a high-consistency pulp sample 12 of interest through a combined system of excitation-collection optics 14, thereby generating scattered light that is collected by the combined excitation-collection optics 14. A portion of the scattered light is gathered by the combined excitation-collection optics 14 and delivered to a detector/analyzer 16 controlled by a computer 18.

Figure 2:
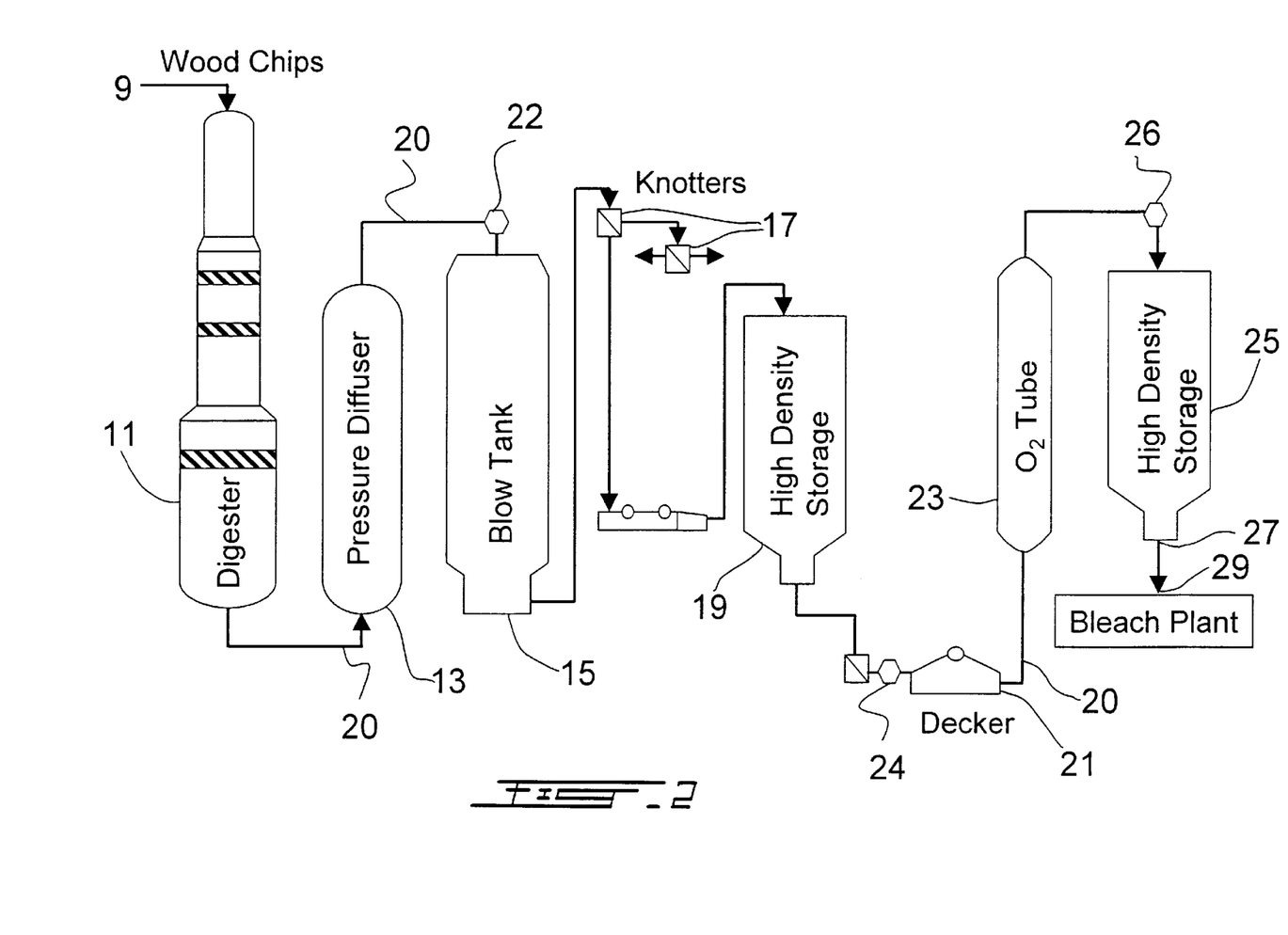
FIG. 2 is a diagrammatic view of a pulping/$O_2$ delignification system, complete with sensing apparatus according to another embodiment of the present invention.

FIG. 2 is a diagrammatic view of a pulping/$O_2$ delignification system, complete with the sensing apparatus previously described in FIG. 1 according to another embodiment of the present invention. Referring to FIG. 2, the pulp sample 12 typically flows through a network of tanks, pipes or conduits 20 forming part of a pulping/$O_2$ delignification system which includes a digestor 11, having an inlet for wood chips 9, a pressure diffuser 13, a blow tank 15, knotters 17, a first high density storage tank 19, a decker 21, an oxygen ($O_2$) tube 23 and a second high density storage tank 25 having an outlet 27 to a bleach plant 29; alternatively the pulp sample 12 could comprise a bypass line which conveys part of the total pulp taken from different locations. In one embodiment of the invention, these locations could be the digester blow line 22, the decker inflow line 24 or the $O_2$ delignification outlet 26. The exact number and location of the sampling points along the network of pipes/conduits 20 may vary from mill to mill. Referring again to FIG. 1, a portion of the scattered light is gathered in both cases by the combined excitation-collection optics 14 and delivered to a detector/analyzer 16 controlled by a computer 18. With the use of either a peak-ratio calculation or a PLS multi-component calibration model, the computer 18 uses and processes the output from detector/analyser 16 to produce a calculated Kappa number 28 representative of the calculated lignin concentration in the pulp sample 12. Variations in the consistency of the pulp sample 12 have been accounted for by the PLS calibration model, and therefore will not interfere with the Kappa-number measurements.

Figure 3:
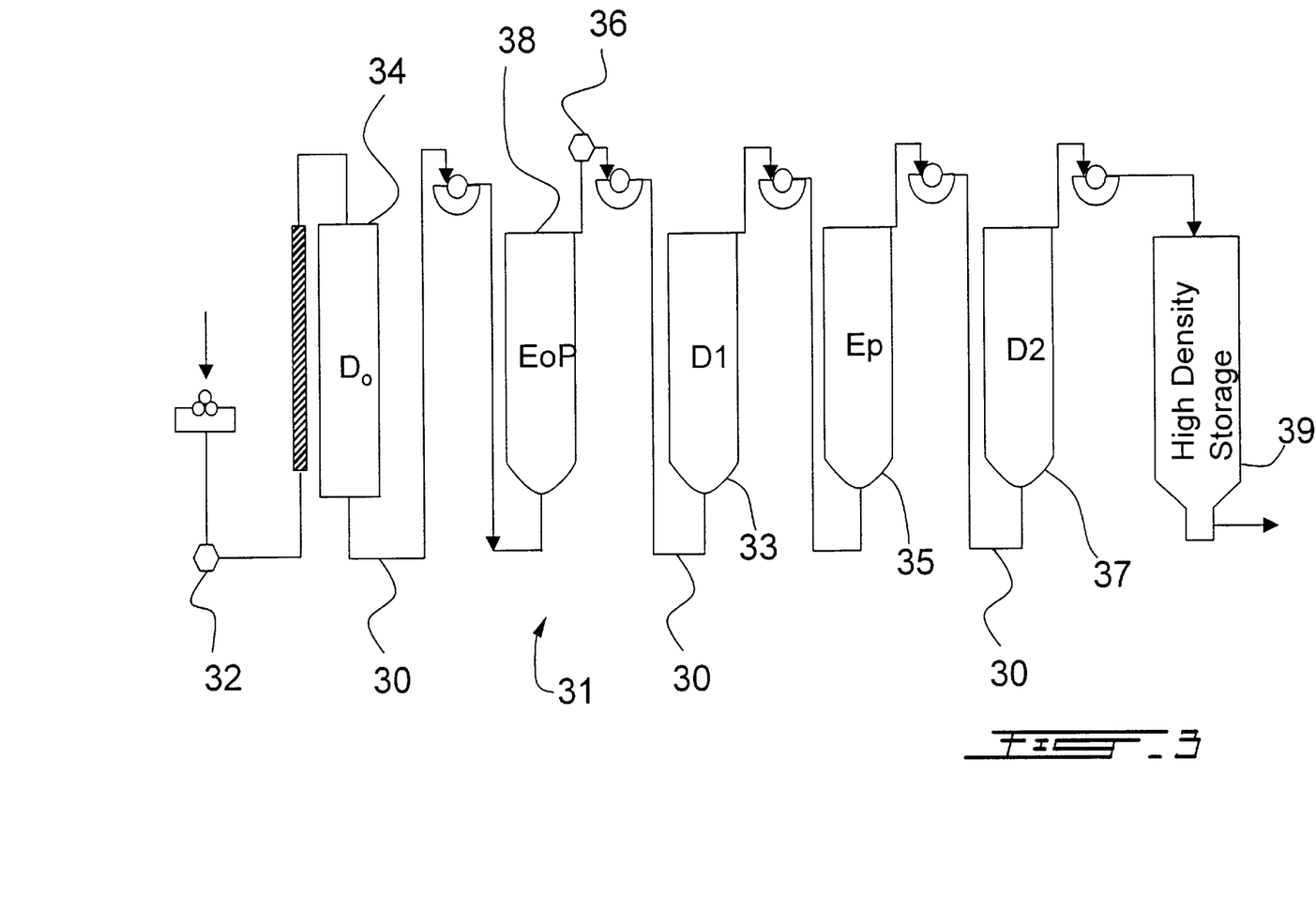
FIG. 3 is a diagrammatic view of a bleaching system, complete with sensing apparatus according to a third embodiment of the present invention.

FIG. 3 is a diagrammatic view of a bleaching system 31, complete with the same sensing apparatus referred to in FIG.

1 according to another embodiment of the present invention. Bleaching system 31, includes a $D_o$ tower 34, an $E_oP$ tower 38, a $D_1$ tower 33, an $E_p$ tower 35, a $D_2$ tower 37 and a high density storage tank 39. In the present embodiment, the pulp sample 12 typically flows through a network of tanks, pipes or conduits 30 forming part of a bleaching system; alternatively the pulp sample 12 could comprise a bypass line which conveys part of the total pulp taken from different locations. In this embodiment of the invention, these locations could be at the inflow line 32 of the Do tower 34, and the outflow line 36 of the $E_oP$ bleaching stage 38. The exact number and location of the sampling points along the network of pipes/conduits 30 may vary from mill to mill. Referring again to FIG. 1, a portion of the scattered light is gathered by the combined excitation-collection optics 14 and delivered to a detector/analyzer 16 controlled by a computer 18. With the use of either a peak-ratio calculation or a PLS multi-component calibration model, the computer 18 uses and processes the output from detector/analyser 16 to produce a calculated Kappa number 28 representative of the calculated lignin concentration in the pulp sample 12. Variations in the consistency of the pulp sample 12 have been accounted for by the PLS calibration model, and therefore will not interfere with the Kappa-number measurements.

Figure 5:
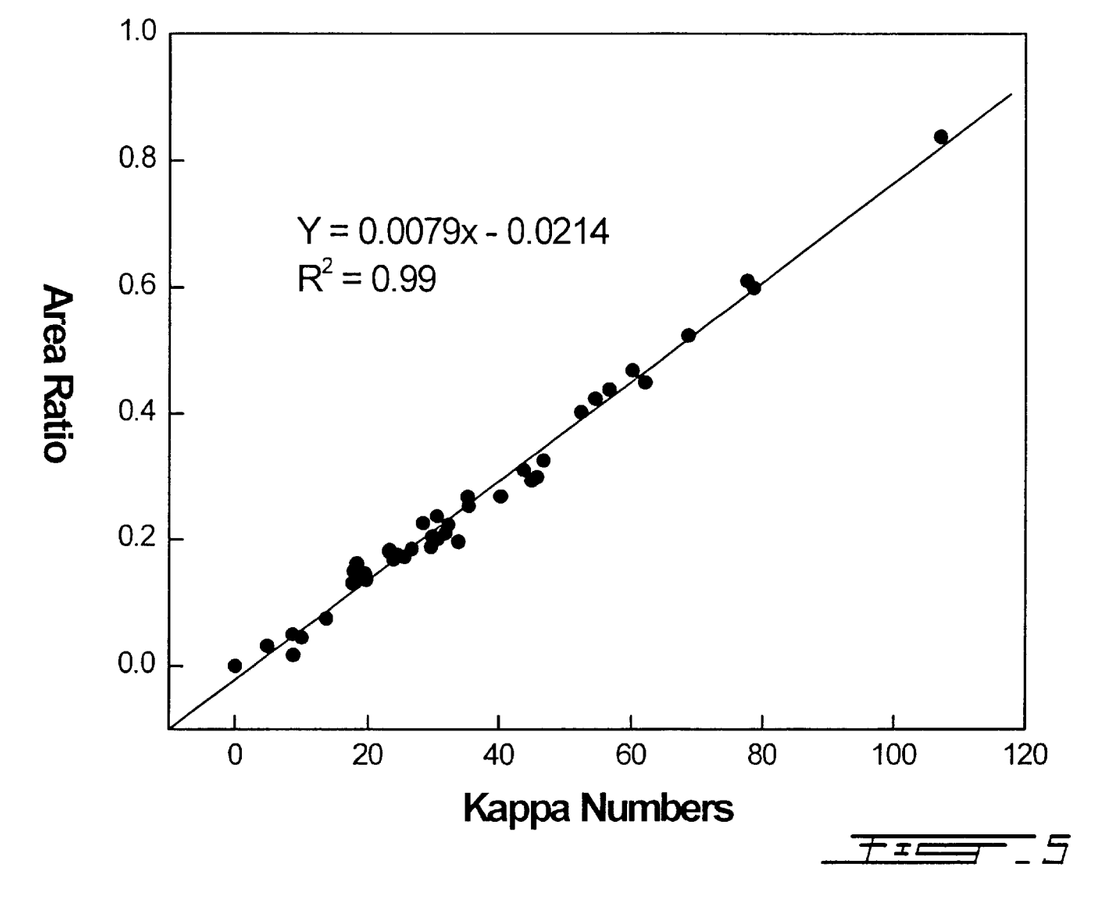
FIG. 5 is a calibration graph of the ratio of the baseline-corrected integrated Raman-scattered light intensity around 1600 $cm^{-1}$ over the baseline-corrected integrated Raman-scattered light intensity around 1100 $cm^{-1}$ versus Kappa number concentration for forty-eight softwood pulps.
Figure 6:
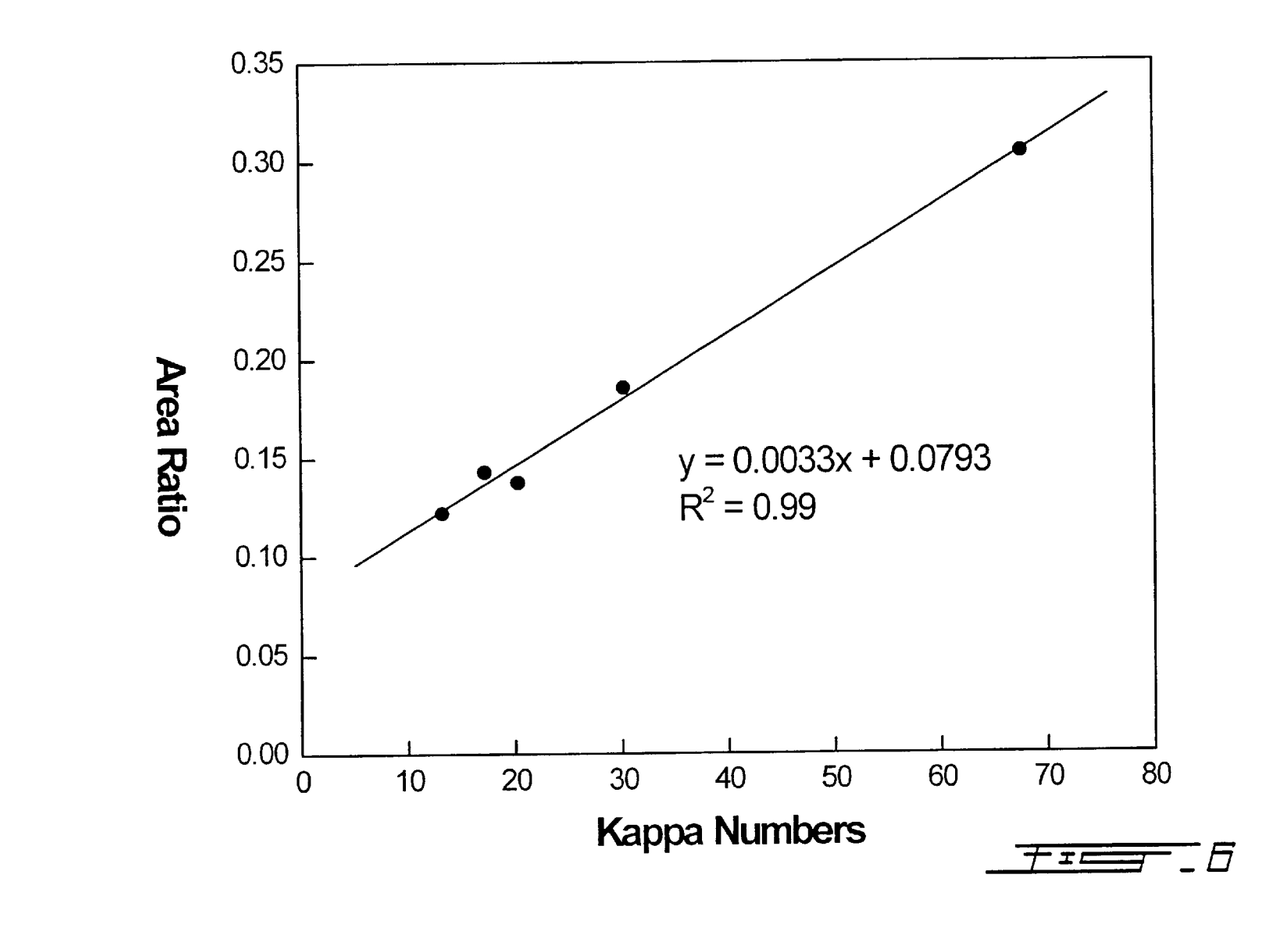
FIG. 6 is a calibration graph of the ratio of the baseline-corrected integrated Raman-scattered light intensity around 1600 $cm^{-1}$ over the baseline-corrected integrated band Raman-scattered light intensity around 1100 $cm^{-1}$ versus Kappa number concentration for five hardwood pulps.
Figure 7:
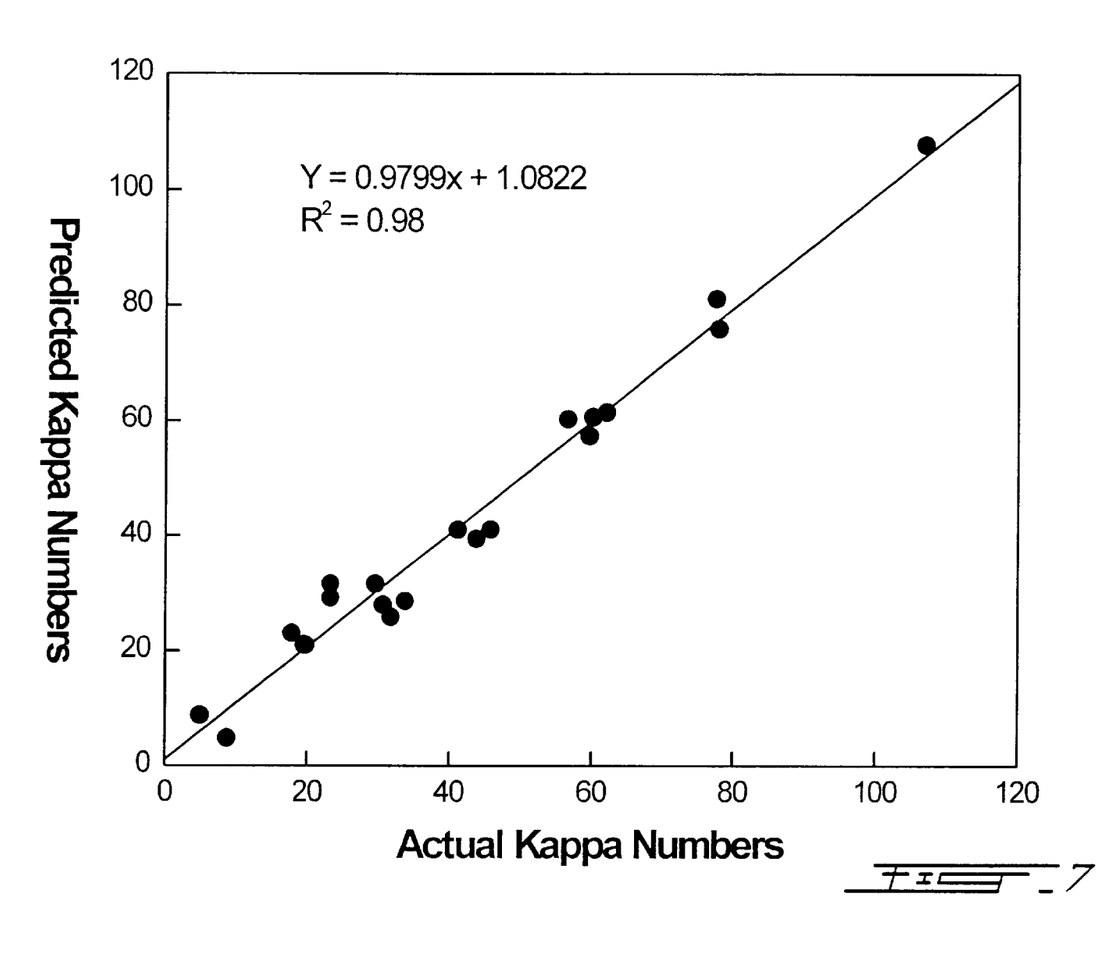
FIG. 7 is a PLS calibration graph of the predicted versus actual Kappa number for the lignin-component PLS calibration model.

As an alternative measure of the lignin concentration, the present invention utilizes the ratio, R, of the Raman-scattered light intensity, I (v), integrated over two wavenumbers ranges, one comprised of higher wavenumbers and the other comprised of lower wavenumbers. Specifically for the data shown in FIG. 5 and FIG. 6, this is determined by:

$$R = \frac{\int_{\lambda=1580}^{\lambda=1640} I(v)\,dv}{\int_{\lambda=1020}^{\lambda=1200} I(v)\,dv}$$

where the limits on the integrals are given in $cm^{-1}$. FIG. 5 and FIG. 6 show that the ratio R provides essentially the same measurement as does the PLS calibration (see FIG. 7).

A combined system of pipes, light guides or infrared fiber-optic cables is used for remote sensing in the recovery system so that liquor can be sampled from multiple locations, thereby minimizing system costs by allowing multiple streams to be analysed by a single Raman apparatus. The computer can then be programmed so as to adjust the operational variables of either the pulping/$O_2$ delignification and/or bleaching systems(s) so as to reduce Kappa number variability. Alternatively, the information received from the computer may be communicated directly to an operator who will perform manual adjustments.

EXPERIMENTAL

Fifty-five kraft pulp samples of various species were prepared by laboratory batch cooks, giving various pulp kappa numbers. Details are given in Table I (softwoods) and Table II (hardwoods). Samples were equilibrated with air by exposing them to room temperature and moisture for several days. The samples were then stored in plastic containers for transportation purposes.

Raman-scattered light intensity measurements were performed with the Kaiser Optical Systems integrated Holoprobe® 785 nm system, which comprises a f/1.8 spectrograph, a 100 mW external cavity stabilized diode laser emitting at 785 nm, a thermoelectrically cooled (−40° C.) charged-coupled device detector, and a fiber-optic probe. The Raman system was equipped with a holographic laser-line rejection filter and a volume holographic transmission grating. Spectral shift coverage was from −50 to 3400 $cm^{-1}$. Spectral resolution was 4 $cm^{-1}$. The laser source is a continuous-wave diode laser with an excitation wavelength of 785 nm. A fiber-optic cable transports the light to a microscope probe; The probe consists of a bundle of nine collection fibers (200 μm core diameter) surrounding a single excitation fiber having a 400-μ diameter. The laser beam goes through a series of mirrors and holographic notch filters before being focused down through the objective lens and onto the sample. With this acquisition mode, the dry pulp sample is placed on a microscope slide under the objective lens. The microscope setup allows one to focus the laser light onto a macro surface of the pulp samples. Typical acquisition time is approximately between 5 to 10 minutes. Exposure times can be set to fill up approximately 60 to 70 percent of the detector (CCD camera with a resolution of 1024×256 pixels). So as to accomplish the desired settings, the laser exposure time is adjusted along with the number of accumulations. Sample analyses was performed with the pulp sample being damp, hand squeezed to remove some of the absorbed water.

The PLS facility provided with the Grams/32™ (Galactic Industry Corp., Salem NH) data processing software package was used for the multi-component calibration step. The composition of the pulp samples is given in Table I and II. All lignin concentrations were verified with standard methods ["T236—Kappa Number of Pulp", TAPPI Standard Methods, TAPPI PRESS, Atlanta; "G. 18—Kappa Number of Pulp", Standard Methods of the Technical Section of the CPPA, Montreal]. For the calibration model, the synthetic-liquor spectra were sorted between two sets, a calibration set and a validation set. Two-thirds of the samples, including all samples that showed concentrations extremes, were incorporated into the calibration set being used for building the spectral model, thereby minimizing the likelihood of outliers. The remainder of the samples were used for verifying the accuracy of the model and validating the calibration. Results obtained with the use of these two calibration models for the mill and validation samples are given in Table III, respectively. These results are discussed in the following examples:

EXAMPLE 1

Figure 4:
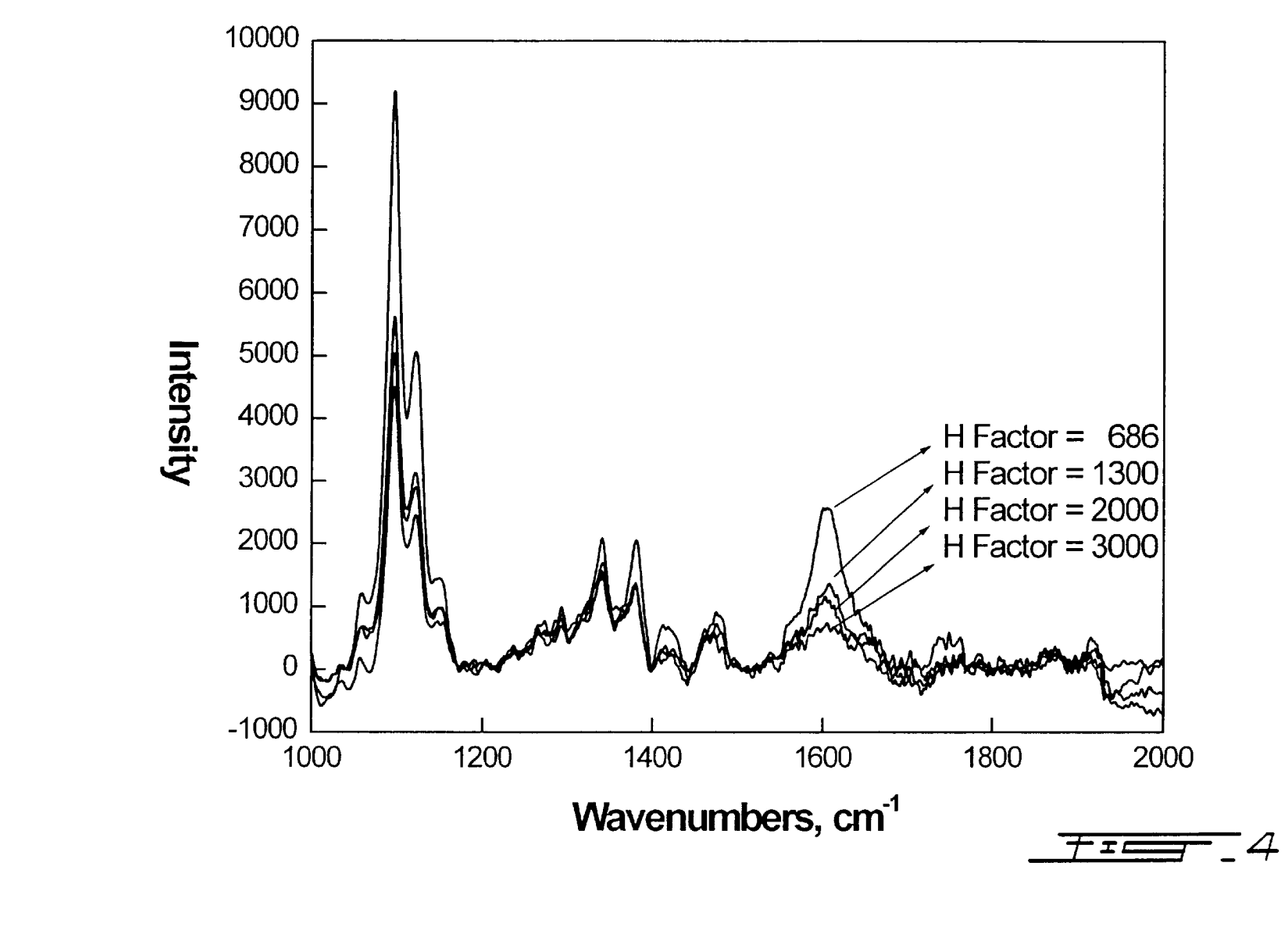
FIG. 4 is a graph of the baseline-corrected visible Raman-scattered light intensity versus wavenumbers showing the change in the baseline-corrected Raman-scattered light intensity for four pulps at increasing H-factors during a cook and having different lignin and cellulose concentrations.

This example discusses results obtained with softwood samples. FIG. 4 shows a graph of the baseline-corrected Raman-scattered light intensity versus wave numbers showing the change in the baseline-corrected Raman scattered-light intensity for four pulps of the same spruce-pine-fir (SPF) mixture, sampled at increasing H-factors and having different lignin and cellulose concentrations. Following a multi-point baseline correction, the original spectra were re-calculated so as to obtain the corrected Raman spectra shown in FIG. 4. For the forty-eight softwood samples listed in TABLE I, the baseline-corrected peaks for cellulose and lignin were then integrated so as to obtain their areas. The ratio of the areas for the peak at 1600 $cm^{-1}$ to that at 1100 $cm^{-1}$ is plotted in FIG. 5 against the Kappa numbers given in TABLE I for these softwood samples. The area for the cellulose peak acts as an internal standard that automatically corrects for the pulp consistency variations found with each sample. Good correlation, with an $R^2$ value of 0.99, is obtained for all types of softwood species. When compared to the results obtained by Ibrahim et al., both the increase in energy and the improved signal to noise ratios allow one to analyze pulp down to lower kappa numbers, despite a strong fluorescence background. Good accuracy is obtained for samples that have a Kappa number within the range of industrial interest, i.e., below 25 for softwoods. Given that lignin content is higher for softwoods than for hardwoods, one would expect the visible-light interference from the lignin-generated fluorescence to be higher than for the results shown by Sun et al. with near-infrared light for hardwood species and by Ibrahim et al. for softwood species. Surprisingly, the exact opposite situation prevails: the standard deviation of the visible-light method is in the order of ±2.5 kappa units for five replicates. This is a considerable improvement when compared to the results shown by Ibrahim et al. and by Sun et al., whereby the standard deviation was found to be ±10 kappa units. The improved lignin content measurement is not anticipated by neither Ibrahim et al. nor by Sun et al.

EXAMPLE 2

This example discusses results obtained with hardwood samples. For five (Nos. 1, 2, 3, 5 and 6) of the eight hardwood samples listed in TABLE II, a multi-point baseline correction was performed, and the original spectra were re-calculated so as to obtain corrected Raman spectra. The baseline-corrected peaks for cellulose and lignin were then integrated so as to obtain their areas. The ratio of the areas for the peak at 1600 cm$^{-1}$ to that at 1100 cm$^{-1}$ is plotted in FIG. 5 against the Kappa numbers given in TABLE II for these five hardwood samples. It was not possible to obtain reliable peak areas for three of the hybrid poplar samples having a high lignin content (Nos. 5, 7 and 8, TABLE II) because of a very strong fluorescence signal. This is not a big disadvantage since the values of Kappa numbers for those samples lie outside the range of industrial interest, i.e., below 15 for hardwoods. In general, stronger fluorescence interference is obtained for hardwoods than for softwoods, a result that is quite surprising given the lower amount of lignin in hardwoods. This finding is not anticipated by Sun et al.

EXAMPLE 3

A one-component PLS calibration was performed with twelve spectra obtained from the samples listed in TABLE I for the purpose of building a calibration that is capable of predicting the Kappa number and/or percent lignin concentration of pulps during pulping and $O_2$ delignification. So as to compensate for consistency variations, Raman-scattered light intensities were normalized to the intensity of the cellulose peak at 1095 cm$^{-1}$. The spectral shift region chosen for building the model was from 1566 to 1656 cm$^{-1}$. The number of factors used for the prediction was three. The PLS method relies on normalized peak-height measurements, and thus is more easily automated than the peak/area method described in Example 1. Although the correlation looks more scattered than the one described in Example 1, the small number of factors needed for the prediction indicate that the model chosen is very robust and can identify/reject outliers. The results shown in TABLE III for five validation samples show good to fair agreement between the predicted values and standard-method values for the Kappa number of each sample. The precision and accuracy of the results is comparable to that obtained in Example I.

EXAMPLE 4

Figure 8:
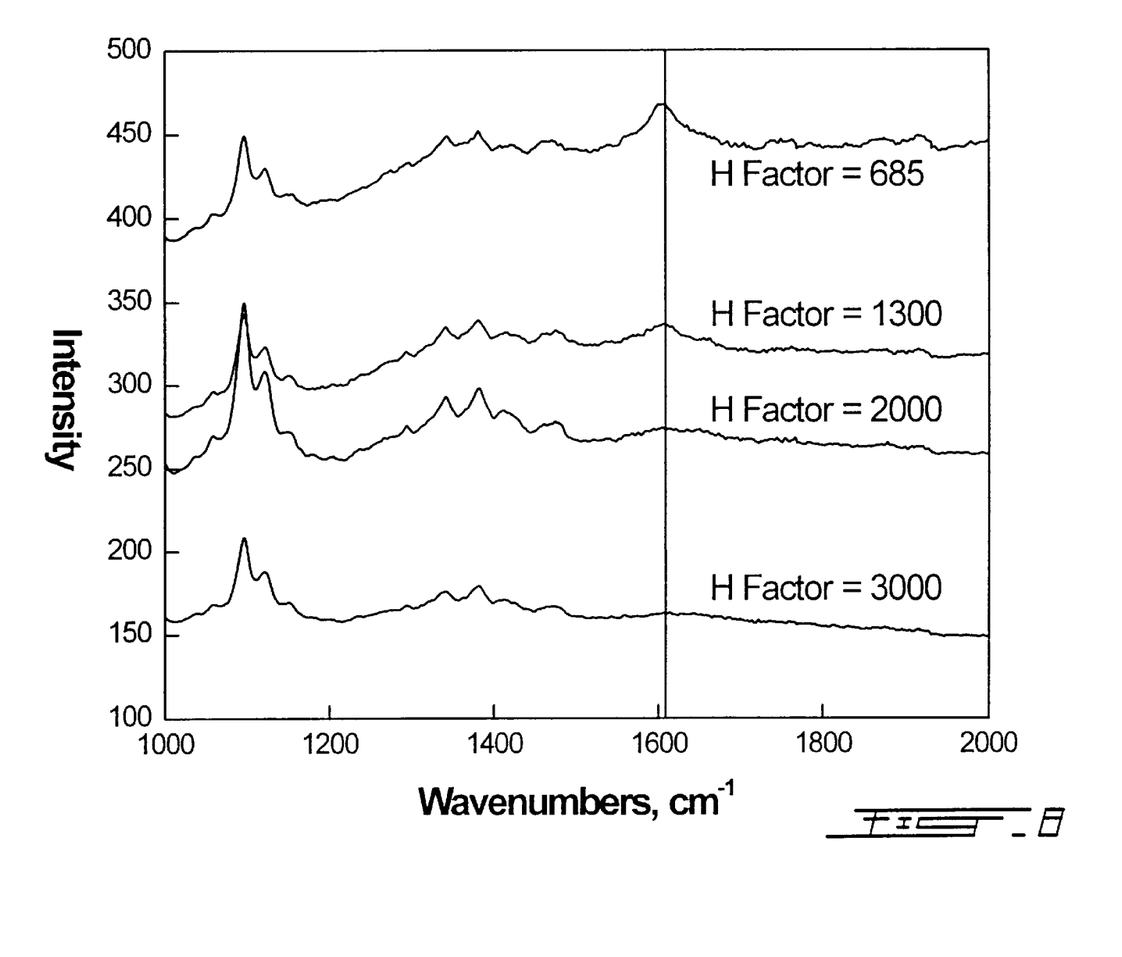
FIG. 8 is a graph of the uncorrected Raman-scattered light intensity versus wavenumbers showing the change in the fluorescence level with decreasing lignin content for four pulps at increasing H-factors during a cook and having different lignin and cellulose concentrations.

The difference in background fluorescence intensity can be clearly observed when examining the Raman spectrum of bleached pulp. FIG. 8 illustrates five visible Raman-scattered light intensity spectra of pulp samples with decreasing Kappa numbers. The fluorescence background decreases with lignin content. In bleached pulp, the baseline is flat and the areas of cellulose peak and of the lignin peak can be easily quantified. The area is obtained by integrating over a fixed region of the spectrum.

From the above examples it can be seen that both softwood and hardwood pulps manufactured during a chemical pulping process can be analysed and that the kappa number, and optionally the residual lignin content, can be measured with the use of various types of partial least-squares (PLS) multivariate calibration. Such a method correlates the spectral behavior for different lignin concentrations in a calibration sample with their actual concentration in that sample. The set of correlations represents a model that can then be used to predict the Kappa number and/or lignin content in an unknown sample. Consequently, by varying at least one process variable, the process can be controlled so that optimal values of the aforesaid parameters are obtained.

TABLE I

Softwood Samples and Kappa Numbers

| Sample No. | Wood Species | Kappa No. | H-Factor |
| --- | --- | --- | --- |
| 1 | D-Fir | 77.6 | 600 |
| 2 | D-Fir | 56.6 | 800 |
| 3 | D-Fir | 45.7 | 1000 |
| 4 | D-Fir | 41.1 | 1200 |
| 5 | D-Fir | 29.5 | 1500 |
| 6 | D-Fir | 23.2 | 2000 |
| 7 | WR Cedar | 107.0 | 450 |
| 8 | WR Cedar | 78.0 | 700 |
| 9 | WR Cedar | 59.6 | 900 |
| 10 | WR Cedar | 43.7 | 1200 |
| 11 | WR Cedar | 31.7 | 1500 |
| 12 | WR Cedar | 23.2 | 2000 |
| 13 | SPF | 62 | 685 |
| 14 | SPF | 30.6 | 1300 |
| 15 | SPF | 19.7 | 2000 |
| 16 | SPF | 8.7 | |
| 17 | SPF | 4.9 | |
| 18 | Lodge Pole | 78.6 | |
| 19 | Lodge Pole | 68.6 | |
| 20 | Lodge Pole | 54.5 | |
| 21 | Lodge Pole | 29.7 | |
| 22 | Lodge Pole | 24.4 | |
| 23 | Lodge Pole | 13.7 | |
| 24 | Lodge Pole | 10 | |
| 25 | Lodge Pole | 8.8 | |
| 26 | Lodge Pole | 0 | |
| 27 | Jack Pine | 60.1 | 1200 |
| 28 | Jack Pine | 33.7 | 1500 |
| 29 | Jack Pine | 19.5 | 1800 |
| 31 | Jack Pine | 18.3 | 1200 |
| 32 | Jack Pine | 17.9 | 1000 |
| 33 | Jack Pine | 17.7 | 1300 |
| 34 | Balsam Fir | 46.5 | 1700 |
| 35 | Balsam Fir | 35.1 | 1000 |
| 36 | Balsam Fir | 28.3 | 1300 |
| 37 | Balsam Fir | 52.4 | 1600 |
| 38 | Black Spruce | 44.9 | 1200 |
| 39 | Black Spruce | 44.9 | 1200 |
| 40 | Black Spruce | 32.2 | 1500 |
| 41 | Black Spruce | 23.8 | 1800 |
| 42 | Black Spruce | 23.8 | 1800 |
| 43 | W. Hemlock | 46.7 | 800 |
| 44 | W. Hemlock | 35.3 | 1100 |
| 45 | W. Hemlock | 26.6 | 1400 |
| 46 | Hemlock | 40.2 | 800 |
| 47 | Hemlock | 30.4 | 1400 |
| 48 | Hemlock | 26.6 | 1800 |

TABLE II

Hardwood Samples and Kappa Numbers

| Sample No. | Wood Species | Kappa No. | H-Factor |
|---|---|---|---|
| 1 | Aspen | 67.7 | 200 |
| 2 | Aspen | 30.2 | 600 |
| 3 | Aspen | 13.2 | 1500 |
| 4 | Hybrid Poplar | 27.9 | |
| 5 | Hybrid Poplar | 20.3 | |
| 6 | Hybrid Poplar | 17.2 | |
| 7 | Hybrid Poplar | 35.3 | |
| 8 | Hybrid Poplar | 24.6 | |

TABLE III

Partial-least Squares Predicted Results of Validation Set

| Sample No. | Wood Species | Actual Kappa | Pred. Kappa |
|---|---|---|---|
| 1 | Jack Pine | 60.1 | 59.1 |
| 2 | Jack Pine | 33.7 | 30.2 |
| 3 | Jack Pine | 20.5 | 22.3 |
| 4 | Balsam Fir | 46.5 | 46.4 |
| 5 | Balsam Fir | 35.1 | 35.1 |
| 6 | Balsam Fir | 28.3 | 26.0 |
| 7 | Western | 46.7 | 47.9 |
| 8 | Western | 35.3 | 34.9 |
| 9 | Lodge Pole | 78.6 | 79.3 |

What is claimed is:

1. A method for determining lignin content in a wood pulp having a kappa number in a range of 5 to 25, during pulping and bleaching operations of a chemical pulp manufacturing process, comprising the steps of:
   a) withdrawing a plurality of high consistency samples of wood pulp having a kappa number in a range of 5 to 25 from a chemical pulp manufacturing process;
   b) subjecting said plurality of samples to a monochromatic visible-light source having a wavelength of 700 to 850 nanometers and allowing the samples to scatter said visible light;
   c) determining the Raman spectrum of the scattered visible light over a predetermined range of wave numbers to produce Raman-scattered light intensity measurements performed with a charge-coupled device; and
   d) comparing the Raman-scattered light intensity measurements of said plurality of samples with the Raman-scattered light intensity measurements shown by known combinations of lignin content, cellulose content and consistency and evaluating the lignin content of said wood pulp therefrom.

2. A method according to claim 1, wherein lignin content is measured using kappa number measurements and there is determined the kappa number of the wood pulp in a range of 5 to 20 kappa.

3. A method according to claim 2, wherein said range is 5 to 15 kappa.

4. A method according to claim 1, wherein step d) comprises correlating by univariate calibration, relationships between said Raman-scattered light intensity measurements of said plurality of samples and said Raman-scattered light intensity measurements shown by said known combinations, for the comparison.

5. A method according to claim 4, including a step of determining at least one of an uncorrected, baseline corrected and an integrated Raman-scattered light intensity, over a predetermined range of wave numbers, shown by different known combinations of lignin content, cellulose content and consistency for said comparing in step d).

6. A method according to claim 1, wherein step d) comprises correlating by multivariate calibration, relationships between said Raman-scattered light intensity measurements of said plurality of samples and said Raman-scattered light intensity measurements shown by said known combinations, for the comparison.

7. A method according to claim 6, including a step of determining at least one of an uncorrected, baseline corrected and an integrated Raman-scattered light intensity, over a predetermined range of wave numbers, shown by different known combinations of lignin content, cellulose content and consistency for said comparing in step d).

8. A method according to claim 1, including a step of determining at least one of an uncorrected, baseline corrected and an integrated Raman-scattered light intensity, over a predetermined range of wave numbers, shown by different known combinations of lignin content, cellulose content and consistency for said comparing in step d).

9. A method according to claim 1, wherein the Raman-scattered light measurements in step c) are carried out within a range of wave number shift situated from 1000 to 2000 $cm^{-1}$ with respect to the excitation frequency.

10. A method according to claim 1, wherein the Raman-scattered light intensity measurements are carried out with spectrophotometry performed with visible-light scattering measurements.

11. A method according to claim 10, wherein said fiber-optic excitation/collection probe is used in said spectrophotometry.

12. A method according to claim 1, wherein the Raman-scattered light intensity measurements are carried out with spectrophotometry performed in a flow-through cell for continuous measurements.

13. A method according to claim 1, wherein the relationships between the Raman-scattering measurements of samples with the Raman-scattering measurements for different known pulp lignin concentrations are obtained with the use of partial least-squares (PLS) multivariate calibration.

14. A method according to claim 1, wherein lignin content is measured using kappa number measurements.

15. A method according to claim 1, wherein step c) is carried out in a time of 5 to 10 minutes.

16. A method according to claim 15, wherein said wood pulp samples of step a) comprise pulp suspension having a consistency of 15% to 30%.

17. A method according to claim 16, wherein said pulp is a hardwood pulp.

18. A method according to claim 16, wherein said pulp is a softwood pulp having a kappa number of 5 to 15.

19. A method according to claim 15, wherein said monochromatic visible-light source has an intensity of at least 100 mW.

20. A method according to claim 1, wherein said monochromatic visible-light source has an intensity of at least 100 mW.

21. A method according to claim 1, wherein said Raman spectrum determined in step c) is a non-Fourier Transform Raman spectrum.

* * * * *

UNITED STATES PATENT AND TRADEMARK OFFICE
CERTIFICATE OF CORRECTION

PATENT NO. : 6,551,451 B2
DATED : April 22, 2003
INVENTOR(S) : Thanh P. Trung et al.

It is certified that error appears in the above-identified patent and that said Letters Patent is hereby corrected as shown below:

<u>Title page, Item [54] and Column 1, lines 1 and 3,</u>
Title, substitute -- LIGNIN -- for "LIQUID"; and substitute -- RAMAN -- for "RAMEN".

Signed and Sealed this

Thirtieth Day of August, 2005

JON W. DUDAS
*Director of the United States Patent and Trademark Office*